United States Patent [19] [11] 4,054,663

Morisawa et al. [45] Oct. 18, 1977

[54] PYRIDINE DERIVATIVES AND THEIR USE AS ANTICOCCIDIAL AGENTS

[75] Inventors: Yasuhiro Morisawa; Mitsuru Kataoka; Noritoshi Kitano; Toshiaki Matsuzawa, all of Tokyo, Japan

[73] Assignee: Sankyo Company Limited, Tokyo, Japan

[21] Appl. No.: 639,697

[22] Filed: Dec. 11, 1975

[30] Foreign Application Priority Data

| | | |
|---|---|---|
| Dec. 23, 1974 | Japan | 49-147908 |
| Mar. 18, 1975 | Japan | 50-32739 |
| May 21, 1975 | Japan | 50-60519 |
| Sept. 5, 1975 | Japan | 50-107822 |

[51] Int. Cl.$^2$ .................... C07D 213/56; A61K 31/44

[52] U.S. Cl. .......................... 424/266; 260/294.8 D; 260/295 R; 260/295 AM; 260/295.5 R; 260/295.5 A

[58] Field of Search ................ 260/295 AM, 295.5 A; 424/266

[56] References Cited

U.S. PATENT DOCUMENTS 4,002,629 1/1977 DeLarge et al. ............ 260/295.5 A

OTHER PUBLICATIONS

Roberts et al., Basic Principles of Organic Chemistry, Benjamin Pub. pp. 799-801, (1965).

*Primary Examiner*—Alan L. Rotman
*Attorney, Agent, or Firm*—Flynn & Frishauf

[57] ABSTRACT

Pyridine derivatives having the formula

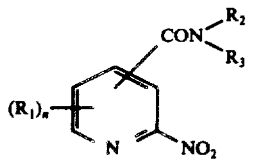

wherein $R_1$ is an alkyl group having 1 to 3 carbon atoms; $R_2$ is hydrogen atom or an alkyl group having 1 to 3 carbon atoms; $R_3$ is hydrogen atom, an alkyl group having 1 to 4 carbon atoms, an alkenyl group having 3 or 4 carbon atoms, an alkyl group having 1 or 2 carbon atoms and hydroxy as a substituent, an alkanoyl group having 1 to 18 carbon atoms, an alkenoyl group having 3 to 11 carbon atoms, an aromatic acyl group having 6 or 10 carbon atoms in the aromatic ring and optionally alkyl, alkoxy, acetylamino, cyano or halogen as a substituent, a heterocyclic acyl group, an alkylcarbamoyl group having 1 to 4 carbon atoms in the alkyl moiety, an allylcarbamoyl group or hydroxy group; $n$ is an integer of 0 to 2 inclusive; and, when $n$ is 2, $R_1$'s may be the same or different; provided that when $R_2$ is said alkyl group having 1 to 3 carbon atoms, $R_3$ is said alkyl group having 1 to 4 carbon atoms.

They are highly effective in the treatment of coccidiosis.

31 Claims, No Drawings

PYRIDINE DERIVATIVES AND THEIR USE AS ANTICOCCIDIAL AGENTS

This invention relates to a new group of pyridine derivatives and their use as an anticoccidial agent.

More particularly, it is concerned with a new pyridine derivative having the formula (I)

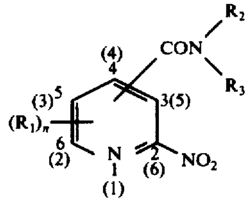

wherein $R_1$ is an alkyl group having 1 to 3 carbon atoms; $R_2$ is hydrogen atom or an alkyl group having 1 to 3 carbon atoms; $R_3$ is hydrogen atom, an alkyl group having 1 to 4 carbon atoms, an alkenyl group having 3 or 4 carbon atoms, an alkyl group having 1 or 2 carbon atoms and hydroxy as a substituent, an alkanoyl group having 1 to 18 carbon atoms, an alkenoyl group having 3 to 11 carbon atoms, an aromatic acyl group having 6 or 10 carbon atoms in the aromatic ring and optionally alkyl, alkoxy acetylamino, cyano or halogen as a substituent, a heterocyclic acyl group, an alkylcarbamoyl group having 1 to 4 carbon atoms in the alkyl moiety, an allylcarbamoyl group or hydroxy group; *n* is an integer of 0 to 2 inclusive; and, when *n* is 2, $R_1$'s may be the same or different; provided that when $R_2$ is said alkyl group having 1 to 3 carbon atoms, $R_3$ is said alkyl group having 1 to 4 carbon atoms.

It is also concerned with a new composition containing, as an active anticoccidial agent, the pyridine derivative (I).

Coccidiosis is a common and widespread disease of poultries, especially chickens and turkeys, and domestic animals such as rabbits, goats, sheep, and cattles, which disease is caused by a kind of protozoa belonging to class Sporozoa, order Coccidia, family Eimeriidae.

Coccidiosis of polutries and domestic animals is caused mainly by the protozoa belonging to genus Eimeria, which disease is classified to an acute type and a chronic one.

The former is caused by such species as *E. tenella* and *E. necatrix*, and the characteristic feature of the disease is a copious bloody discharges from the ceca and small intestine of diseased poultries, which often die within a day or two.

The latter is caused by such species as *E. acervulina, E. maxima, E. brunetti, E. praecox, E. hagani, E. mitis* and *E. mivati*, and the characteristic feature of the disease is that the mortality of diseased poultries is rather few, whereas a poor weight gain, a reduced feed efficiency and a reduced efficiency of egg-production are commonly observed.

Infant rabbits as well as cattles, sheep and goats sometimes cause severe lesions by parasite Eimeria within their levers and intestines.

Oocysts of coccidia are excreted from an infected animal with feces, and spores having infectivity are produced within 24 - 48 hours under suitable conditions, which spores enter into a non-infected animal orally.

Oocysts grow at first asexually within the cells of the caecum or small intestine of the host animal, during which time the heaviest symptoms is observed. Then, they grow sexually and are excreted with the feces of the host animal and they exhibit an awful communicability.

The elimination or control of coccidiosis is, therefore, of paramount importance particularly in the poultry industry.

There have been proposed much preventive and curative methods for coccidiosis. One of them is a development in chemotherapeutic agents such as sulfa drugs, arsenic compounds, nitrofuran derivatives, nitrophenide, Nicarbazine, Zoalane, pyrimidine derivatives (anti-thiamines), quinoline derivatives, guanidine derivatives, various antibiotics and so on.

But they have some defects; i.e. weak activity, narrow anti-protozoal spectrum, lack of security for aninals or acquired resistance to the drugs by protozoa, respectively. Therefore, treatment with the hither-to-known anticoccidial agent is not satisfactory.

We have previously found that the pyridinol derivatives having the formula

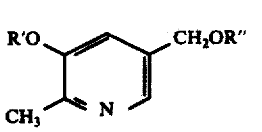

wherein R' and R" may be the same or different and each represents hydrogen atom, a lower alkyl group, an aralkyl group, an aliphatic, an aromatic or a heterocyclic acyl group, an alkoxycarbonyl group, an aralkoxycarbonyl group, an aryloxycarbonyl group; a N-substituted carbamoyl group, a N-substituted thiocarbamoyl group, a phosphono group show anticoccidial activities against species of the genus Eimeria, especially against *E. acervulina*, as disclosed and claimed in our co-pending Japanese Patent Applications No. 105090/1972 and No. 41111/1973. Also, we have found that pyridine derivatives having the formula

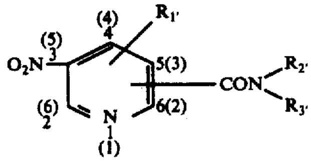

wherein $R_1'$ is hydrogen atom, a halomethyl group or methyl group; $R_2'$ is hydrogen atom or an alkyl group of 1-3 carbon atoms; $R_3'$ is hydrogen atom, an alkyl group of 1-3 carbon atoms, allyl group, an alkyl group having 2 or 3 carbon atoms and alkoxy of 1 or 2 atoms as a substituent, an alkyl group having 1-3 carbon atoms and hydroxy as a substituent, an alkanoy group of 1-18 carbon atoms, a haloacetyl group, an alkenoyl group of 3-11 carbon atoms, an aromatic acyl group, a heterocyclic acyl group, an N-alkylcarbamoyl group of 1-4 carbon atoms in the alkyl moiety or hydroxy group; provided that when $R_2'$ is said alkyl group of 1-3 carbon atoms, $R_3'$ is said alkyl group of 1-3 carbon atoms and inorganic acid addition salts thereof show a prominent anticoccidial activity against all species of the genus Eimeria, especially against *Eimeria tenella*, which is known most pathogenic and lives in the caecum of host, and also they are highly effective against those strains resistant to known various thiamine type anticoccidial agents widely utilized in the art, as disclosed and claimed in our co-pending British Patent Application No. 32833/75 filed on Aug. 6, 1975.

As a result of our further studies on pyridine derivatives and their anticoccidial activities, we have found that the new pyridine derivatives (I) show a remarkably high anticoccidial activity against all species belonging to the genus Eimeria and they also are highly effective against those strains resistant to known various thiamine type anticoccidial agents.

It is, accordingly, a primary object of this invention to provide a new class of the pyridine derivatives (I) which are useful as anticoccidial agents.

It is another object of this invention to provide an anticoccidial composition which are highly effective in treating and preventing coccidiosis.

Another objects will become apparent from the following detailed description of this invention.

In the above formula (I), $R_1$ may be exemplified by hydrogen atom, methyl, ethyl, n-propyl, isopropyl group. $R_2$ may be exemplified by hydrogen atom, methyl, ethyl, n-propyl or isopropyl group. $R_3$ may be exemplified by hydrogen atom, methyl, ethyl, n-propyl, isopropyl, n-butyl, iso-butyl, sec-butyl, tert-butyl, allyl, 3-butenyl, hydroxymethyl, 2-hydroxyethyl, formyl, acetyl, propionyl, butyryl, isobutyryl, valeryl, isovaleryl, 2-methylbutyryl, pivaloyl, hexanoyl, 2-methyl-n-valeryl, 3-methyl-n-valeryl, 4-methyl-n-valeryl, 2-ethyl-n-butyryl, heptanoyl, octanoyl, 2-ethylhexanoyl, nonanoyl, 3,3,5-trimethylhexanoyl, decanoyl, undecanoyl, n-lauroryl, myristoyl, pentadecanoyl, palmitoyl, stearoyl, acryloyl, crotonoyl, 3-butenoyl, methacryloyl, tigloyl, sorboyl, 10-undecanoyl, oleoyl, benzoyl, 2,3-dimethoxybenzoyl, 3,4-dimethoxybenzoyl, 3,5-dimethylbenzoyl, o-, m-, p-toluoyl, o-, m-, p-chlorobenzoyl, o-, m-, p-bromobenzoyl, p-methoxybenzoyl, o-, m-, p-acetylaminobenzoyl, o-, m-, p-cyanobenzoyl, 2-ethoxy-4-acetylaminobenzoyl, 2-ethoxy-4-dimethylaminobenzoyl, 2-methoxy-4-acetylaminobenzoyl, 2-furoyl, 2-thenoyl, isonicotinoyl, nicotinoyl, N-methylcarbamoyl, N-ethylcarbamoyl, N-n-propylcarbamoyl, N-isopropylcarbamoyl, N-n-butylcarbamoyl, N-isobutylcarbamoyl, N-t-butylcarbamoyl, N-allylcarbamoyl or hydroxy group.

In one aspect of this invention, there is provided a new class of the pyridine derivatives (I).

Among the pyridine compounds of the formula (I) which may be employed in this invention, as a preferable group may be mentioned those pyridine compounds of the formula (I) wherein $R_2$ is hydrogen atom or an alkyl group having 1 or 2 carbon atoms and $R_3$ is hydrogen atom, an alkyl group having 1 or 2 carbon atoms, allyl group, hydroxymethyl group, an alkanoyl group having 1 to 9 carbon atoms, an alkenoyl group having 3 or 4 carbon atoms, a benzoyl group which may be substituted with methyl, methoxy or halogen, 2-thenoyl group, an alkylcarbamoyl group having 1 or 2 carbon atoms in the alkyl moiety or hydroxy group; provided that when $R_2$ is said alkyl group having 1 or 2 carbon atoms, $R_3$ is said alkyl group having 1 or 2 carbon atoms.

More preferable group of the pyridine derivatives of the formula (I) is those wherein $R_2$ is hydrogen atom or an alkyl group having 1 or 2 carbon atoms and $R_3$ is hydrogen atom, an alkyl group having 1 or 2 carbon atoms, an alkanoyl group having 1 to 9 carbon atoms or a benzoyl group which may be substituted with one of methyl, methoxy, chlorine and bromine; provided that when $R_2$ is said alkyl group having 1 or 2 carbon atoms, $R_3$ is said alkyl group having 1 or 2 carbon atoms.

Still more preferably are those pyridine derivatives of the formula (I) wherein the group

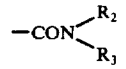

is attached to the pyridine ring, at the 4-position thereof, n is 0 or 1, $R_1$ is methyl group, $R_2$ is hydrogen atom or an alkyl group having 1 or 2 carbon atoms and $R_3$ is hydrogen atom, an alkyl group having 1 or 2 carbon atoms, allyl group, hydroxymethyl group, an alkanoyl group having 1 to 9 carbon atoms, an alkenoyl group having 3 or 4 carbon atoms, a benzoyl group which may be substituted with methyl, methoxy or halogen, 2-thenoyl group, an alkylcarbamoyl group having 1 or 2 carbonn atoms in the alkyl moiety or hydroxy group; provided that when $R_2$ is said alkyl group having 1 or 2 carbon atoms.

Of the pyridine derivatives of the formula (I), representative examples thereof are listed below, but they are not intended to be limiting the scope of this invention.

1. 2-Nitroisonicotinamide
2. 2-Nitroisonicotinohydroxamic acid
3. N-Allyl 2-Nitroisonicotinamide
4. N-Methyl 2-Nitroisonicotinamide
5. N-Ethyl 2-Nitroisonicotinamide
6. N-n-Propyl 2-Nitroisonicotinamide
7. N-i-Propyl 2-Nitroisonicotinamide
8. N-n-Butyl 2-Nitroisonicotinamide
9. N-i-Butyl 2-Nitroisonicotinamide
10. N-sec-Butyl 2-Nitroisonicotinamide
11. N-Hydroxymethyl 2-Nitroisonicotinamide
12. N-(2-Hydroxyethyl) 2-Nitroisonicotinamide
13. N,N-Dimethyl 2-Nitroisonicotinamide
14. N,N-Diethyl 2-Nitroisonicotinamide
15. N,N-Di-n-propyl 2-Nitroisonicotinamide
16. N,N-Di-i-propyl 2-Nitroisonicotinamide
17. N-Ethyl-N-methyl 2-Nitroisonicotinamide
18. N-Methyl-N-propyl 2-Nitroisonicotinamide
19. N-Ethyl-N-propyl 2-Nitroisonicotinamide
20. N-Formyl 2-Nitroisonicotinamide
21. N-Acetyl 2-Nitroisonicotinamide
22. N-Propionyl 2-Nitroisonicotinamide
23. N-Butyryl 2-Nitroisonicotinamide
24. N-Isobutyryl 2-Nitroisonicotinamide
25. N-Valeryl 2-Nitroisonicotinamide
26. N-Isovaleryl 2-Nitroisonicotinamide
27. N-(2-methylbutyryl) 2-Nitroisonicotinamide
28. N-Pivaloyl 2-Nitroisonicotinamide
29. N-Hexanoyl 2-Nitroisonicotinamide
30. N-(2-Methylvaleryl) 2-Nitroisonicotinamide
31. N-(3-Methylvaleryl) 2-Nitroisonicotinamide
32. N-(4-Methylvaleryl) 2-Nitroisonicotinamide
33. N-(2-Ethylbutyryl) 2-Nitroisonicotinamide
34. N-Heptanoyl 2-Nitroisonicotinamide
35. N-Octanoyl 2-Nitroisonicotinamide
36. N-(2-Ethylhexanoyl) 2-Nitroisonicotinamide
37. N-Nonanoyl 2-Nitroisonicotinamide
38. N-(3,3,5-Trimethylhexanoyl) 2-Nitroisonicotinamide
39. N-Decanoyl 2-Nitroisonicotinamide
40. N-Undecanoyl 2-Nitroisonicotinamide 41. N-Lauroyl 2-Nitroisonicotinamide
42. N-Myristoyl 2-Nitroisonicotinamide
43. N-Pentadecanoyl 2-Nitroisonicotinamide
44. N-Palmitoyl 2-Nitroisonicotinamide
45. N-Stearoyl 2-Nitroisonicotinamide
46. N-Acryloyl 2-Nitroisonicotinamide
47. N-Crotonoyl 2-Nitroisonicotinamide
48. N-(3-Butenoyl) 2-Nitroisonicotinamide
49. N-Methacryloyl 2-Nitroisonicotinamide
50. N-Tigloyl 2-Nitroisonicotinamide
51. N-Sorboyl 2-Nitroisonicotinamide
52. N-Benzoyl 2-Nitroisonicotinamide
53. N-(2,3-Dimethoxybenzoyl) 2-Nitroisonicotinamide
54. N-(3,4-Dimethoxybenzoyl) 2-Nitroisonicotinamide
55. N-(3,5-Dimethylbenzoyl) 2-Nitroisonicotinamide
56. N-(o-Toluoyl) 2-Nitroisonicotinamide
57. N-(m-Toluoyl) 2-Nitroisonicotinamide
58. N-(p-Toluoyl) 2-Nitroisonicotinamide
59. N-(o-Chlorobenzyl) 2-Nitroisonicotinamide
60. N-(m-Chlorobenzoyl) 2-Nitroisonicotinamide
61. N-(p-Chlorobenzoyl) 2-Nitroisonicotinamide
62. N-(o-Bromobenzoyl) 2-Nitroisonicotinamide
63. N-(m-Bromobenzoyl) 2-Nitroisonicotinamide
64. N-(p-Bromobenzoyl) 2-Nitroisonicotinamide
65. N-(p-Methoxybenzoyl) 2-Nitroisonicotinamide
66. N-(o-Acetylaminobenzoyl) 2-Nitroisonicotinamide
67. N-(m-Acetylaminobenzoyl) 2-Nitroisonicotinamide
68. N-(p-Acetylaminobenzoyl) 2-Nitroisonicotinamide
69. N-(p-Cyanobenzoyl) 2-Nitroisonicotinamide
70. N-(m-Cyanobenzoyl) 2-Nitroisonicotinamide
71. N-(2-Ethoxy-4-acetylaminobenzoyl) 2-Nitroisonicotinamide
72. N-(2-Methoxy-4-acetylaminobenzoyl) 2-Nitroisonicotinamide
73. N-(2-Furoyl) 2-Nitroisonicotinamide
74. N-(2-Thenoyl) 2-Nitroisonicotinamide
75. N-Isonicotinoyl 2-Nitroisonicotinamide
76. N-Nictinoyl 2-Nitroisonicotinamide
77. 4-(4-Methylallophanoyl)-2-nitropyridine
78. 4-(4-Ethylallophanoyl)-2-nitropyridine
79. 4-(4-n-Proppylallophanoyl)-2-nitropyridine
80. 4-(4-Isopropylallophanoyl)-2-nitropyridine
81. 4-(4-n-Butylallophanoyl)-2-nitropyridine
82. 4-(4-Isobutylallophanoyl)-2-nitropyridine
83. 4-(4-Allylallophanoyl)-2-nitropyridine
84. 6-Methyl-2-nitroisonicotinamide
85. 6-Methyl-2-nitroisonicotinohydroxamic acid
86. N-Allyl 6-Methyl-2-nitroisonicotinamide
87. N-Methyl 6-Methyl-2-nitroisonicotinamide
88. N-Ethyl 6-Methyl-2-nitroisonicotinamide
89. N-n-Propyl 6-Methyl- 2-nitroisonicotinamide
90. N-i-Propyl 6-Methyl-2-nitroisonicotinamide
91. N-n-Butyl 6-Methyl-2-nitroisonicotinamide
92. N-i-Butyl 6-Methyl-2-nitroisonicotinamide
93. N-sec-Butyl 6-Methyl-2-nitroisonicotinamide
94. N-Hydroxymethyl 6-Methyl-2-nitroisonicotinamide
95. N-(2-Hydroxyethyl) 6-Methyl-2-nitroisonicotinamide
96. N,N-Dimethyl 6-Methyl-2-nitroisonicotinamide
97. N,N-Diethyl 6-Methyl-2-nitroisonicotinamide
98. N,N-Di-n-Propyl 6-Methyl-2-nitroisonicotinamide
99. N,N-Di-i-Propyl 6-Methyl-2-nitroisonicotinamide
100. N-Ethyl-N-methyl 6-Methyl-2-nitroisonicotinamide
101. N-Methyl-N-propyl 6-Methyl-2-nitroisonicotinamide
102. N-Ethyl-N-propyl 6-Methyl-2-nitroisonicotinamide
103. N-Formyl 6-Methyl-2-nitroisonicotinamide
104. N-Acetyl 6-Methyl-2-nitroisonicotinamide
105. N-Propionyl 6-Methyl-2-nitroisonicotinamide
106. N-Butyryl 6-Methyl-2-nitroisonicotinamide
107. N-Isobutyryl 6-Methyl-2-nitroisonicotinamide
108. N-Valeryl 6-Methyl-2-nitroisonicotinamide
109. N-Isovaleryl 6-Methyl-2-nitroisonicotinamide
110. N-(2-Methylbutyryl) 6-Methyl-2-nitroisonicotinamide
111. N-Pivaloyl 6-Methyl-2-nitroisonicotinamide
112. N-Hexanoyl 6-Methyl-2-nitroisonicotinamide
113. N-(2-Methylvaleryl) 6-Methyl-2-nitroisonicotinamide
114. N-(3-Methylvaleryl) 6-Methyl-2-nitroisonicotinamide
115. N-(4-Methylvaleryl) 6-Methyl-2-nitroisonicotinamide
116. N-Heptanoyl 6-Methyl-2-nitroisonicotinamide
117. N-Octanoyl 6-Methyl-2-nitroisonicotinamide
118. N-(2-Ethylhexanoyl) 6-Methyl-2-nitroisonicotinamide
119. N-Nonanoyl 6-Methyl-2-nitroisonicotinamide
120. N-Lauroyl 6-Methyl-2-nitroisonicotinamide
121. N-Myristoyl 6-Methyl-2-nitroisonicotinamide
122. N-Palmitoyl 6-Methyl-2-nitroisonicotinamide
123. N-Stearoyl 6-Methyl-2-nitroisonicotinamide
124. N-Acryloyl 6-Methyl-2-nitroisonicotinamide
125. N-Crotonoyl 6-Methyl-2-nitroisonicotinamide
126. N-(3-Butenoyl) 6-Methyl-2-nitroisonicotinamide
127. N-Methacryloyl 6-Methyl-2-nitroisonicotinamide
128. N-Tigloyl 6-Methyl-2-nitroisonicotinamide
129. N-Sorboyl 6-Methyl-2-nitroisonicotinamide
130. N-Benzoyl 6-Methyl-2-nitroisonicotinamide
131. N-(2,3-Dimethoxybenzoyl) 6-Methyl-2-nitroisonicotinamide
132. N-(2,4-Dimethoxybenzoyl) 6-Methyl-2-nitroisonicotinamide
133. N-(3,5-Dimethylbenzoyl) 6-Methyl-nitroisonicotinamide
134. N-(o-Toluoyl) 6-Methyl-2-nitroisonicotinamide
135. N-(m-Toluoyl) 6-Methyl-2-nitroisonicotinamide
136. N-(p-Toluoyl) 6-Methyl-2-nitroisonicotinamide
137. N-(o-Chlorobenzoyl) 6-Methyl-2-nitroisonicotinamide
138. N-(m-Chlorobenzoyl) 6-Methyl-2-nitroisonicotinamide
139. N-(p-Chlorobenzoyl) 6-Methyl-2-nitroisonicotinamide
140. N-(o-Bromobenzoyl) 6-Methyl-2-nitroisonicotinamide
141. N-(m-Bromobenzoyl) 6-Methyl-2-nitroisonicotinamide
142. N-(p-Bromobenzoyl) 6-Methyl-2-nitroisonicotinamide
143. N-(p-Methoxybenzoyl) 6-Methyl-2-nitroisonicotinamide
144. N-(o-Acetylaminobenzoyl) 6-Methyl-2-nitroisonicotinamide
145. N-(m-Acetylaminobenzoyl) 6-Methyl-2-nitroisonicotinamide
146. N-(p-Acetylaminobenzoyl) 6-Methyl-2-nitroisonicotinamide
147. N-(p-Cyanobenzoyl) 6-Methyl-2-nitroisonicotinamide
148. N-(m-Cyanobenzoyl) 6-Methyl-2-nitroisonicotinamide
149. N-(2-Ethoxy-4-acetylaminobenzoyl) 6-Methyl-2-nitroisonicotinamide 150. N-(2-Methoxy-4-acetylaminobenzoyl) 6-Methyl-2-nitroisonicotinamide
151. N-(2-Furoyl) 6-Methyl-2-nitroisonicotinamide
152. N-(2-Thenoyl) 6-Methyl-2-nitroisonicotinamide
153. N-Isonicotinoyl 6-Methyl-2-nitroisonicotinamide
154. N-Nicotinoyl 6-Methyl-2-nitroisonicotinamide
155. 6-Methyl-4-(4-methylallophanoyl)-2-nitropyridine
156. 4-(4-Ethylallophanoyl)-6-methyl-2-nitropyridine
157. 6-Methyl-4-(4-n-propylallophanoyl)-2-nitropyridine
158. 4-(4-Isopropylallophanoyl)-6-methyl-2-nitropyridine
159. 4-(4-n-Butylallophanoyl)-6-methyl-2-nitropyridine
160. 4-(4-Isobutylallophanoyl)-6-methyl-2-nitropyridine
161. 4-(4-allylallophanoyl)-6-methyl-2-nitropyridine
162. 3-Methyl-2-nitroisonicotinamide
163. 3-Methyl-2-nitroisonicotinohydroxamic acid
164. 6-Nitronicotinamide
165. N-Methyl 6-Nitronicotinamide
166. N-Ethyl 6-Nitronicotinamide
167. N-n-Propyl 6-Nitronicotinamide
168. N-i-Propyl 6-Nitronicotinamide
169. N-n-Butyl 6-Nitronicotinamide
170. N-i-Butyl 6-Nitronicotinamide
171. N-Hydroxymethyl 6-Nitronicotinamide
172. N-(2-Hydroxyethyl) 6-Nitronicotinamide
173. N,N-Dimethyl 6-Nitronicotinamide
174. N,N-Diethyl 6-Nitronicotinamide
175. N,N-Di-n-propyl 6-Nitronicotinamide
176. N-Ethyl-N-methyl 6-Nitronicotinamide
177. N-Methyl-N-propyl 6-Nitronicotinamide
178. N-Acetyl 6-Nitronicotinamide
179. N-Propionyl 6-Nitronicotinamide
180. N-Butyryl 6-Nitronicotinamide
181. N-Isobutyryl 6-Nitronicotinamide
182. N-Valeryl 6-Nitronicotinamide
183. N-Isovaleryl 6-Nitronicotinamide
184. N-Hexanoyl 6-Nitronicotinamide
185. N-Heptanoyl 6-Nitronicotinamide
186. N-Octanoyl 6-Nitronicotinamide
187. N-Nonanoyl 6-Nitronicotinamide
188. N-Lauroyl 6-Nitronicotinamide
189. N-Palmitoyl 6-Nitronicotinamide
190. N-Crotonoyl 6-Nitronicotinamide
191. N-Benzoyl 6-Nitronicotinamide
192. N-(o-Toluoyl) 6-Nitronicotinamide
193. N-(m-Toluoyl) 6-Nitronicotinamide
194. N-(p-Toluoyl) 6-Nitronicotinamide
195. N-(o-Chlorobenzoyl) 6-Nitronicotinamide
196. N-(m-Chlorobenzoyl) 6-Nitronicotinamide
197. N-(p-Chlorobenzoyl) 6-Nitronicotinamide
198. N-(p-Methoxybenzoyl) 6-Nitronicotinamide
199. N-(2-Thenoyl) 6-Nitronicotinamide
200. 6-Nitronicotinohydroxamic Acid
201. 5-(4-Methylallophanoyl)-2-nitropyridine
202. 5-(4-Ethylallophanoyl)-2-nitropyridine
203. 5-(4-n-Propylallophanoyl)-2-nitropyridine
204. 5-(4-Isopropylallophanoyl)-2-nitropyridine
205. 5-(4-n-Butylallophanoyl)-2-nitropyridine
206. 4-Methyl-6-nitronicotinamide
207. N-Methyl 4-Methyl-6-nitronicotinamide
208. N-Ethyl 4-Methyl--6-nitronicotinamide
209. N,N-Dimethyl 4-Methyl-6-nitronicotinamide
210. N,N-Diethyl 4-Methyl-6-nitronicotinamide
211. N,N-Di-n-propyl 4-Methyl-6-nitronicotinamide
212. N-Ethyl-N-methyl 4-Methyl-6-nitronicotinamide
213. N-Acetyl 4-Methyl-6-nitronicotinamide
214. N-Propionyl 4-Methyl-6-nitronicotinamide
215. N-Butyryl 4-Methyl-6-nitronicotinamide
216. N-Isobutyryl 4-Methyl-6-nitronicotinamide
217.N-Valeryl 4-Methyl-6-nitronicotinamide
218. N-Isovaleryl 4-Methyl-6-nitronicotinamide
219. N-Pivaloyl 4-Methyl-6-nitronicotinamide
220. N-Hexanoyl 4-Methyl-6-nitronicotinamide
221. N-Heptanoyl 4-Methyl-6-nitronicotinamide
222. N-Octanoyl 4-Methyl-6-nitronicotinamide
223. N-Nonanoyl 4-Methyl-6-nitronicotinamide
224. N-Myristoyl 4-Methyl-6-nitronicotinamide
225. N-Crotonoyl 4-Methyl-6-nitronicotinamide
226. 4-Methyl-6-nitro-2-pyridinecarboxamide
227. 2,4-Dimethyl-6-nitronicotinamide
228. N-Methyl 2,4-Dimethyl-6-nitronicotinamide
229. N-Ethyl 2,4-Dimethyl-6-nitronicotinamide
230. N-n-Propyl 2,4-Dimethyl-6-nitronicotinamide
231. N,N-Dimethyl 2,4-Dimethyl-6-nitronicotinamide
232. N,N-Diethyl 2,4-Dimethyl-6-nitronicotinamide
233. N,N-Di-n-Propyl 2,4-Dimethyl-6-nitronicotinamide
234. N-Ethyl-N-methyl 2,4-Dimethyl-6-nitronicotinamide
235. N-Acetyl 2,4-Dimethyl-6-nitronicotinamide
236. N-Propionyl 2,4-Dimethyl-6-nitronicotinamide
237. N-Butyryl 2,4-Dimethyl-6-nitronicotinamide
238. N-Isobutyryl 2,4-Dimethyl-6-nitronicotinamide
239. N-Valeryl 2,4-Dimethyl-6-nitronicotinamide
240. N-Isovaleryl 2,4-Dimethyl-6-nitronicotinamide
241. N-Pivaloyl 2,4-Dimethyl-6-nitronicotinamide
242. N-Hexanoyl 2,4-Dimethyl-6-nitronicotinamide
243. N-Heptanoyl 2,4-Dimethyl-6-nitronicotinamide
244. N-Octanoyl 2,4-Dimethyl-6-nitronicotinamide
245. N-Methyl 3-Methyl-2-nitroisonicotinamide
246. N-Ethyl 3-Methyl-2-nitroisonicotinamide
247. N-Acetyl 3-Methyl-2-nitroisonicotinamide
248.N-Propionyl 3-Methyl-2-nitroisonicotinamide
249. N-Butyryl 3-Methyl-2-nitroisonicotinamide
250. N-Isobutyryl 3-Methyl-2-nitroisonicotinamide
251. N-Valeryl 3-Methyl-2-nitroisonicotinamide
252. 6-Ethyl-2-nitroisonicotinamide
253. N-Methyl 6-Ethyl-2-nitroisonicotinamide
254. N-Ethyl 6-Ethyl-2-nitroisonicotinamide
255. N,N-Dimethyl 6-Ethyl-2-nitroisonicotinamide
256. N,N-Diethyl 6-Ethyl-2-nitroisonicotinamide
257. N-Ethyl-N-methyl 6-Ethyl-2-nitroisonicotinamide
258. N-Hydroxymethyl 6-Ethyl-2-nitroisonicotinamide
259. N-Acetyl 6-Ethyl-2-nitroisonicotinamide
260. N-Propionyl 6-Ethyl-2-nitroisonicotinamide
261. N-Butyryl 6-Ethyl-2-nitroisonicotinamide
262. N-Isobutyryl 6-Ethyl-2-nitroisonicotinamide
263. N-Valeryl 6-Ethyl-2-nitroisonicotinamide
264. N-Isovaleryl 6-Ethyl-2-nitroisonicotinamide
265. N-Hexanoyl 6-Ethyl-2-nitroisonicotinamide
266. N-Octanoyl 6-Ethyl-2-nitroisonicotinamide
267. N-Benzoyl 6-Ethyl-2-nitroisonicotinamide
268. N-(o-Toluoyl) 6-Ethyl-2-nitroisonicotinamide
269. N-(m-Toluoyl) 6-Ethyl-2-nitroisonicotinamide
270. N-(p-toluoyl) 6-Ethyl-2-nitroisonicotinamide
271. N-(p-Chlorobenzoyl) 6-Ethyl-2-nitroisonicotinamide
272. 6-Propyl-2-nitroisonicotinamide
273. N-Methyl 6-Propyl-2-nitroisonicotinamide
274. N,N-Dimethyl 6-Propyl-2-nitroisonicotinamide
275. N,N-Diethyl 6-Propyl-2-nitroisonicotinamide
276. N-Acetyl 6-Propyl-2-nitroisonicotinamide
277. N-Propionyl 6-Propyl-2-nitroisonicotinamide
278. N-Hydroxymethyl 4-Methyl-6-nitronicotinamide
279. 4-Methyl-6-nitronicotinohydroxamic Acid 280. N-Benzoyl 4-Methyl-6-nitronicotinamide
281. N-(o-Toluoyl) 4-Methyl-6-nitronicotinamide
282. N-(m-Toluoyl) 4-Methyl-6-nitronicotinamide
283. N-(p-Toluoyl)4-Methyl-6-nitronicotinamide
284. N-(o-Chlorobenzoyl) 4-Methyl-6-nitronicotinamide
285. N-(m-Chlorobenzoyl) 4-Methyl-6-nitronicotinamide
286. N-(p-Chlorobenzoyl) 4-Methyl-6-nitronicotinamide
287. N-(p-Methoxybenzoyl) 4-Methyl-6-nitronicotinamide
288. N-(2-Thenoyl) 4-Methyl-6-nitronicotinamide
289. 4-Methyl-3-(4-methylallophanoyl)-6-nitropyridine
290. 3-(4-Ethylallophanoyl)-4-methyl-6-nitropyridine
291. 4-Methyl-3-(4-n-propylallophanoyl)--6-nitropyridine
292. 3-(4-Isopropylallophanoyl)-4-methyl-6-nitropyridine
293. 4-Ethyl-6-nitronicotinamide
294. N-Methyl 4-Ethyl-6-nitronicotinamide
295. N-Ethyl 4-Ethyl-6-nitronicotinamide
296. N,N-Dimethyl 4-Ethyl-6-nitronicotinamide
297. N,N-Diethyl 4-Ethyl-6-nitronicotinamide
298. N-Acetyl 4-Ethyl-6-nitronicotinamide
299. N-Propionyl 4-Ethyl-6-nitronicotinamide
300. N-Butyryl 4-Ethyl-6-nitronicotinamide
301. N-Isobutyryl 4-Ethyl-6-nitronicotinamide
302. N-Valeryl 4-Ethyl-6-nitronicotinamide
303. N-Hexanoyl 4-Ethyl-6-nitronicotinamide
304. N-Octanoyl 4-Ethyl-6-nitronicotinamide
305. 6-Nitro-4-propyl-nicotinamide
306. 2-Methyl-6-nitronicotinamide
307. N-Methyl 2-Methyl-6-nitronicotinamide
308. N-Ethyl 2-Methyl-6-nitronicotinamide
309. N,N-Dimethyl 2-Methyl-6-nitronicotinamide
310. N,N-Diethyl 2-Methyl-6-nitronicotinamide
311. N-Ethyl-N-methyl 2-Methyl-6-nitronicotinamide
312. N-Acetyl 2-Methyl-6-nitronicotinamide
313. N-Propionyl 2-Methyl-6-nitronicotinamide
314. N-Butyryl 2-Methyl-6-nitronicotinamide
315. N-Isobutyryl 2-Methyl-6-nitronicotinamide
316. N-Valeryl 2-Methyl-6-nitronicotinamide
317. N-Hexanoyl 2-Methyl-6-nitronicotinamide
318. N-Octanoyl 2-Methyl-6-nitronicotinamide
319. N-Hydroxymethyl 2-Methyl-6-nitronicotinamide
320. 5-Methyl-6-nitronicotinamide
321. N-Methyl 5-Methyl-6-nitronicotinamide
322. N-Ethyl 5-Methyl-6-nitronicotinamide
323. N,N-Dimethyl 5-Methyl-6-nitronicotinamide
324. N,N-Diethyl 5-Methyl-6-nitronicotinamide
325. N-Acetyl 5-Methyl-6-nitronicotinamide
326. N-Propionyl 5-Methyl-6-nitronicotinamide
327. N-Butyryl 5-Methyl-6-nitronicotinamide
328. N-Isobutyryl 5-Methyl-6-nitronicotinamide
329. N-Valeryl 5-Methyl-6-nitronicotinamide
330. N-Hexanoyl 5-Methyl-6-nitronicotinamide
331. N-Octanoyl 5-Methyl-6-nitronicotinamide
332. N-Hydroxymethyl 5-Methyl-6-nitronicotinamide
333. N-Benzoyl 5-Methyl-6-nitronicotinamide
334. N-(o-Toluoyl) 5-Methyl-6-nitronicotinamide
335. N-(m-Toluoyl) 5-Methyl-6-nitronicotinamide
336. N-(p-Toluoyl) 5-Methyl-6-nitronicotinamide
337. N-(p-Chlorobenzoyl) 5-Methyl-6-nitronicotinamide
338. N-(p-Methoxybenzoyl) 5-Methyl-6-nitronicotinamide
339. N-(2-Thenoyl) 5-Methyl-6-nitronicotinamide
340. N-(o-Chlorobenzoyl) 5-Methyl-6-nitronicotinamide
341. N-(m-Chlorobenzoyl) 5-Methyl-6-nitronicotinamide
342. N-(p-Bromobenzoyl) 5-Methyl-6-nitronicotinamide
343. 4,5-Dimethyl-6-nitronicotinamide
344. N-Methyl 4,5-Dimethyl-6-nitronicotinamide
345. N-Ethyl 4,5-Dimethyl-6-nitronicotinamide
346. N,N-Dimethyl 4,5-Dimethyl-6-nitronicotinamide
347. N,N-Diethyl 4,5-Dimethyl-6-nitronicotinamide
348. N-Acetyl 4,5-Dimethyl-6-nitronicotinamide
349. N-Propionyl 4,5-Dimethyl-6-nitronicotinamide
350. N-Butyryl 4,5-Dimethyl-6-nitronicotinamide
351. N-Isobutyryl 4,5-Dimethyl-6-nitronicotinamide
352. N-Valeryl 4,5-Dimethyl-6-nitronicotinamide
353. N-Isovaleryl 4,5-Dimethyl-6-nitronicotinamide
354. N-Hexanoyl 4,5-Dimethyl-6-nitronicotinamide
355. N-Heptanoyl 4,5-Dimethyl-6-nitronicotinamide
356. N-Octanoyl 4,5-Dimethyl-6-nitronicotinamide
357. N-Hydroxymethyl 4,5-Dimethyl-6-nitronicotinamide
358. 5-Methyl-2-nitroisonicotinamide
359. 2-Nitronicotinamide
360. 4-Methyl-2-nitronicotinamide
361. N-Methyl 2-nitronicotinamide
362. N-Ethyl 2-nitronicotinamide
363. N,N-Dimethyl 2-nitronicotinamide
364. N,N-Diethyl 2-nitronicotinamide
365. N-Acetyl 2-nitronicotinamide
366. N-Methyl 4-Methyl-2-nitronicotinamide
367. N-Ethyl 4-Methyl-2-nitronicotinamide
368. N-Acetyl 4-Methyl-2-nitronicotinamide
369. N-Propionyl 4-Methyl-2-nitronicotinamide
370. 6-Nitro-2-pyridinecarboxamide
371. N-Methyl 6-Nitro-2-pyridinecarboxamide
372. N,N-Dimethyl 6-Nitro-2-pyridinecarboxamide
373. N,N-Diethyl 6-Nitro-2-pyridinecarboxamide
374. N-Acetyl 6-Nitro-2-pyridinecarboxamide
375. N-Propionyl 6-Nitro-2-pyridinecarboxamide
376. 4-Methyl-6-nitro-2-pyridinecarboxamide
377. N-Methyl 4-Methyl-6-nitro-2-pyridinecarboxamide
378. N-Ethyl 4-Methyl-6-nitro-2-pyridinecarboxamide
379. N,N-Dimethyl 4-Methyl-6-nitro-2-pyridinecarboxamide
380. N,N-Diethyl 4-Methyl-6-nitro-2-pyridinecarboxamide
381. N-Acetyl-4-Methyl-6-nitro-2-pyridinecarboxamide
382. N-Propionyl 4-Methyl-6-nitro-2-pyridinecarboxamide
383. N-3-Butenyl 2-Nitroisonicotinamide
384. N-3-Butenyl 6-Methyl-2-nitroisonicotinamide
385. 6-Methyl-2-nitronicotinamide
386. 4,6-Dimethyl-2-nitronicotinamide
387. 4-Ethyl-5-methyl-6-nitronicotinamide
388. N-Methyl 5-Methyl-2-nitroisonicotinamide
389. N-Ethyl 5-Methyl-2-nitroisonicotinamide
390. N,N-Dimethyl 5-Methyl-2-nitroisonicotinamide
391. N,N-Diethyl 5-Methyl-2-nitroisonicotinamide
392. N-Acetyl 5-Methyl-2-nitroisonicotinamide
393. N-Propionyl 5-Methyl-2-nitroisonicotinamide
394. N-Butyryl 5-Methyl-2-nitroisonicotinamide
395. N-Hexanoyl 5-Methyl-2-nitroisonicotinamide
396. N-Octanoyl 5-Methyl-2-nitroisonicotinamide It is to be noted that the above-defined Compound Nos. will be frequently referred to hereinbelow.

Of the above-listed compounds, there are mentioned the following compounds as a preferable group in view of their anticoccidial activities.

Compound Nos. 1, 4, 5, 11, 13, 14, 17, 21, 22, 23, 24, 25, 26, 29, 35, 47, 52, 56, 57, 58, 59, 60, 61, 65, 74, 84, 85, 87, 88, 96, 97, 104, 105, 106, 107, 108, 109, 112, 117, 130, 134, 135, 136, 137, 138, 139, 143, 162, 206, 226.

The still more preferable group of the above-listed compounds are as follows:

Compound Nos. 1, 4, 5, 11, 13, 17, 21, 24, 35, 47, 52, 56, 58, 61, 65, 74, 84, 85, 88, 96, 97, 105, 143, 162, 206, 226.

The most preferable group of the above-listed compounds are as follows:

Compound Nos. 1, 4, 5, 11, 13, 17, 21, 24, 35, 47, 52, 56, 57, 58, 61, 65, 74, 84, 85, 88, 96, 97, 105, 143, 162.

The above-mentioned Compound Nos. are frequently referred to hereinbelow.

The pyridine compounds of the formula (I) which may be employed in the present invention may be prepared, for instance, by any of the processes as illustratively shown hereunder.

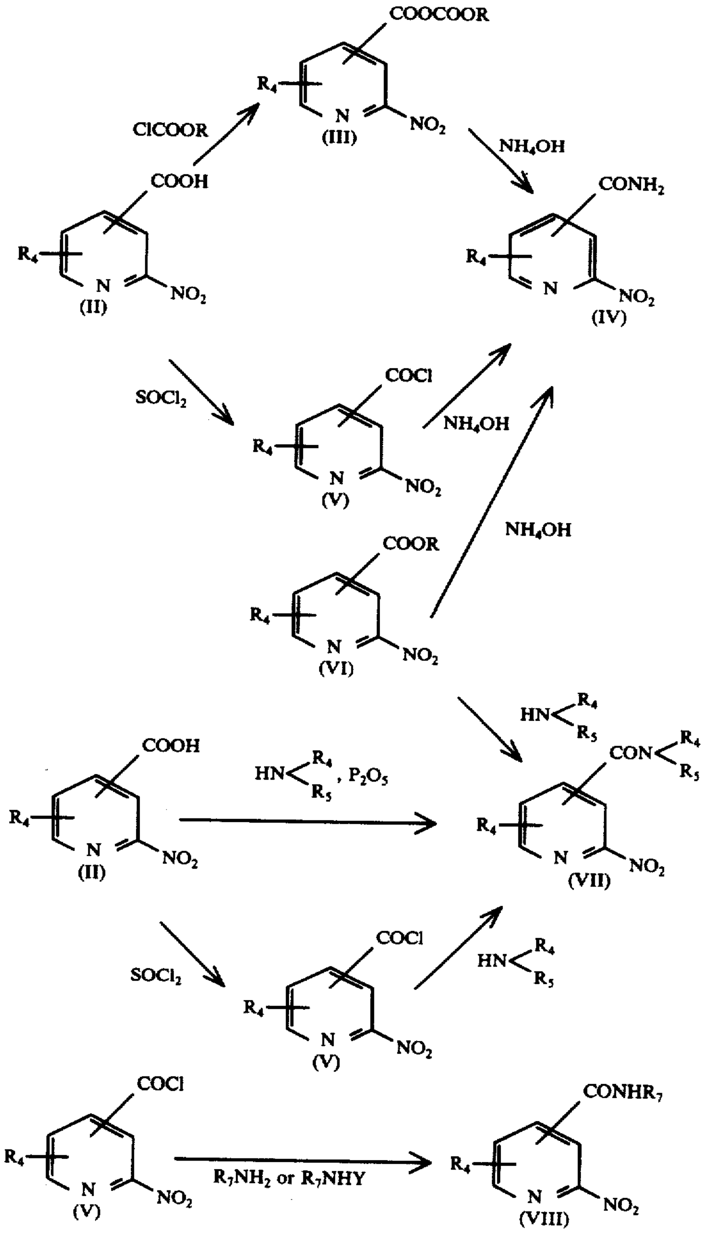

-continued

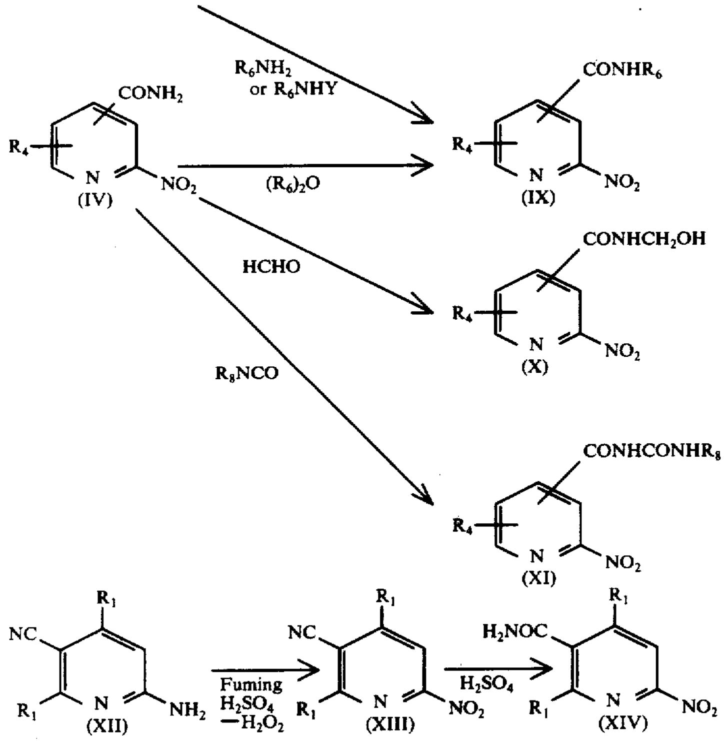

In the above formula, R is a lower alkyl group; $R_4$ and $R_5$ may be the same or different and each represents a lower alkyl group or $R_4$ is hydrogen atom and $R_5$ is a lower alkyl group, a lower alkenyl group, a lower alkyl group substituted with hydroxy; $R_6$ is an alkanoyl group or an alkenoyl group; $R_7$ is an aromatic acyl group or a heterocyclic acyl group; $R_8$ is a lower group; Y is sodium or potassium atom; and $R_1$ is as defined above.

The processes as illustrated above will be more fully explained hereinbelow.

1. (II) → (III) → (IV)

The compounds (IV) may be prepared from the compounds (II) by reacting with the chloroformate and then contacting with ammonia.

2. (II) → (V) → (IV)

The compounds (IV) may be prepared by reacting the compounds (II) with thionyl chloride to give an acid chloride and then bringing the acid chloride into contact with ammonia.

3. (VI) → (IV)

The compounds (IV) may also be prepared from the compounds (VI) by contacting with ammonia.

4. (II) → (VII)

The compounds (VII) may be prepared from the compounds (II) by contacting with the amine in the presence of $P_2O_5$, usually at 30° - 100° C., if necessary, in the presence of a suitable organic solvent.

5. (VI) → (VII)

The compounds (VII) may also be prepared from the compounds (VI) by reacting with the amine.

6. (II) → (V) → (VII)

The compounds (VII) may also be prepared from the compounds (II) by reacting with thionyl chloride and then with the amine.

7. (V) → (VIII)

The compounds (VIII) may be prepared from the compounds (V) by contacting sodium or potassium salt of the acid amide in the presece of a suitable solvent at room temperature or by contacting the acid amide in pyridine.

8. (V) → (IX)

The compounds (IX) may be prepared from the compounds (V) by contacting sodium or potassium salt of the acid amide in the presence of a suitable solvent at room temperature or by contacting the acid amide in pyridine.

9. (IV) → (IX)

The comppunds (IX) may be prepared from the compounds (IV) by contacting with the acid anhydride at 10° - 150° C.

10. (IV) → (X)

The compounds (X) may be prepared from the compounds (IV) by heating with formalin at 50° - 100° C.

11. (IV) → (XI)

The compounds (XI) may be prepared from the compounds (IV) by heating with the isocyanate at 100° - 180° C. in the presence or absence of a suitable solvent.

In the above-mentioned processes, recovery and purification of the desired product may be easily effected by a conventional method and the starting materials (II) and (VI) are disclosed in J. Am, Chem. Soc., 76, 3167 (1954) and Aus. J. Chem., 24, 377 (1971), respectively or can be easily prepared according to the methods taught therein.

12. (XII) → (XIII) → (XIV)

The compounds (XIV) may be prepared from the compounds (XII) [Bull. Chem. Soc. Jap., 42, 2319(1969)] by reacting with fuming sulfuric acid -hydrogen peroxide and then treating with sulfuric acid. -

The preparation of the present pyridine derivative (I) will be more fully illustrated by the following examples, but these examples are not to be limiting the scope of this invention.

EXAMPLE 1

2-Nitroisonicotinamide (Compound No. 1)

A mixture of 400 mg. of methyl 2-nitroisonicotinate and 2 ml. of 28% aqueous ammonia were stirred at room temperature for 1 hour. The solvent was distilled off, and the residue was recrystallized from ethanol-ether to give 348 mg. of the desired product.

M.P. (decomposition) 173° C

EXAMPLE 2

6-Methyl-2-nitroisonicotinamide (Compound No. 84)

A mixture of 1.0 g of 6-methyl-2-nitroisonicotinic acid and 20 ml. of thionyl chloride was refluxed for 3 hours, Excess thionyl chloride was distilled off and the residual oil was slowly added to 15 ml. of cool conc. ammonia. The resulting mixture was allowed to stand for 1 hour, adjusted to pH 7.0 with dil. hydrochloric acid and extracted with ethyl acetate.

The extract was washed with water, dried over anhydrous sodium sulfate and then the solvent was distilled off in vacuo. The residue was recrystallized from ethyl acetate - n-hexane to give 0.5 g. of the desired product.

M.P. 227°-228° C.

Following the above-mentioned process, there were synthesized the compounds below.

| Compound No. | M.P. (° C.) |
|---|---|
| 162 | 127 - 128 |
| 164 | 216 - 219 (dec.) |
| 206 | 178 - 179.5 |
| 226 | 184 - 185 |
| 359 | 193 - 195 |
| 360 | 189 |

EXAMPLE 3

N-Methyl 2-nitroisonicotinamide (Compound No. 4)

1.2 g. of 2-nitroisonicotinic acid and 30 ml. of thionyl chloride were refluxed for 3 hours. An excess of thionyl chloride was distilled off, and the residual oil was dissolved in 5 ml of chloroform. To this solution was added under cooling aqueous methylamine solution (40%) and the resulting mixture was then stirred for one hour.

The precipitated crystals were collected by filtration and recrystallized from ethyl acetate - n-hexane to yield 0.688 g. of the desired compound.

M.P. 131° - 133° C.

Following the above-mentioned process, there were synthesized the compounds below.

| Compound No. | M.P. (° C.) |
|---|---|
| 5 | 65 - 67 |
| 6 | 90 - 91 |
| 3 | 97 - 98 |
| 12 | 141 - 143 |
| 13 | 131 - 132 |
| 17 | 84 - 86 |
| 86 | 87 - 88 |
| 88 | 72 - 74 |
| 95 | 142 - 144 |
| 96 | 61 - 63 |
| 85 | 150 - 152 (dec.) |
| 165 | 181 - 182 |
| 167 | 113 - 115 |
| 169 | 105 |
| 172 | 151 - 152 |
| 174 | 84 - 85 |
| 200 | 158 - 160 |
| 371 | 126 - 127 |
| 372 | 85 - 86 |
| 378 | 116 - 117 |
| 379 | 112 - 113 |
| 367 | 158 - 159 |
| 246 | 80 - 82 |

EXAMPLE 4

N-Ethyl 2-nitroisonicotinamide (Compound No. 5)

A mixture of 500 mg. of methyl 2-nitroisonicotinate and 2 ml. of 70% ethylamine was stirred at room temperature for 5 hours. The reaction mixture was extracted with ethyl acetate. The extract was washed with water, dried and then the solvent was distilled off. The crystalline residue was recrystallized from ethyl acetate - n-hexane to give 328 mg. of the desired product.

M.P. 65° - 67° C.

EXAMPLE 5

N,N-Diethyl 6-methyl-2-nitroisonicotinamide (Compound No. 97)

To a mixture of 1.0 g. of 6-methyl-2-nitroisonicotinic acid, 20 ml. of chloroform and 3 ml. of diethylamine was added 7.0 g. of phosphorus pentoxide with stirring. The resulting mixture was refluxed for 1 hour. After cooling, the chloroform layer was separated and poured into 20 ml. of water. The resulting mixture was neutralized with sodium hydrogencarbonate and the chloroform layer was separated, dried ever anhydrous sodium sulfate and the chloroform was distilled off in vacuo. The residual oil was gradually crystallized and then recrystallized from ethyl acetate - n-hexane to give 0.6 g. of the desired product.

M.P. 90° - 91° C.

EXAMPLE 6

N-(m-Toluoyl) 2-nitroisonicotinamide (Compound No. 57)

1.8 g. of 2-nitroisonicotinic acid and 30 ml. of thionyl chloride were refluxed for 3 hours. An excess of thionyl chloride was distilled off to leave 2-nitroisonicotinoyl chloride as an oil. The obtained acid chloride was added to 5 ml. of pyridine at −15° C., and to the resulting solution was added 1.5 g. of m-toluylamide. The mixture was stirred at room temperature for one hour and the solvent was evaporated at 40° C under reduced pressure. The residue was then purified by silica gel chromatography and recrystallized from ethyl acetate-n-hexane to yield 250 mg. of the desired crystals.

M.P. 147° - 148° C.

Following the above process, there were synthesized the following compounds.

| Compound No. | M.P. (° C.) |
|---|---|
| 61 | 180 - 181 |
| 65 | 174 - 176 |
| 52 | 169 - 171 |
| 58 | 194 - 196 (dec.) |
| 56 | 191 - 192 |
| 74 | 164 - 165 |
| 143 | 205 - 205 (dec.) |
| 197 | 180 - 182 |
| 194 | 182 - 184 |
| 199 | 176 - 178 |

EXAMPLE 7

N-Octanoyl 2-nitroisonicotinamide (Compounds No. 35)

To a mixture of 0.8 g. of 2-nitroisonicotinamide and 2.4 ml. of n-octanoic anhydride were added two drops of conc. sulfuric acid, and the mixture was stirred at room temperature for 16 hours. The reaction solution was poured into ice-water, and the resulting mixture was made weak-alkaline with 5% sodium hydrogencarbonate and extracted with ethyl acetate. The extract was washed with water, dried and the solvent was evaporated. The residue was purified by silica gel chromatography and recrystallized from ethyl acetate - n-hexane to yield 1.36 g. of the desired white crystals.

M.P. 108° - 110° C.

Following the above-mentioned process, there were synthesized the compounds set out below.

| Compound No. | M.P. (° C.) |
|---|---|
| 21 | 181 - 183 |
| 24 | 153 - 155 |
| 47 | 152 - 153 |
| 105 | 104 - 106 |
| 178 | 175 - 177 (dec.) |
| 185 | 114 - 116 |
| 190 | 187 - 189 |
| 374 | 130 - 131 |
| 235 | 137 - 139 |
| 213 | 151 - 152 |
| 214 | 139 - 140 |
| 215 | 147 - 148 |
| 222 | 130 - 131.3 |

EXAMPLE 8

N-Hydroxymethyl 2-nitroisonicatinamide (Compound No. 11)

0.8 g. of 2-nitroisonicotinamide and 2 ml. of 37% formalin were stirred in 2 ml. of dimethylformamide at 110° C for 2 hours. After cooling, to this solution was added ice-water, and the mixture was extracted with ethyl acetate. The extract was washed with water, dried and the solvent was evaporated yielding crystals. The crystals obtained were recrystallized from ethyl acetate to give 0.6 g. of pale yellow crystals.

M.P. 128° - 130° C.

EXAMPLE 9

4-(4-Isopropylallophanoyl)-2-nitropyridine (Compound No. 80)

To 30 ml. of toluene were added 0.8 g of 2-nitroisonicotinamide and 1.7 g. of isopropyl isocyanate, and the mixture was refluxed for 6 hours. The reaction mixture was cooled and filtered removing 0.4 g. of the insoluble starting material. The filtrate was concentrated, and the residue was purified by silica gel chromatography and recrystallized from ethyl acetate - n-hexane to yield 0.08 g. of the desired product.

M.P. 132° - 133° C.

Following the above-mentioned process, there were synthesized the compounds set out below.

| Compound No. | M.P. (° C.) |
|---|---|
| 78 | 196 - 198 |
| 202 | 190 |

EXAMPLE 10

2,4-Dimethyl-6-nitronicotinamide (Compound No. 227)

To a solution of 24 ml. of 30% fuming sulfuric acid and 12 ml. of 30% hydrogen peroxide was added dropwise with stirring and cooling in a dry ice-ethanol bath a solution of 2.0 g. of 6-amino-3-cyano-2,4-dimethylpyridine in 10 ml. of conc. sulfuric acid. The resulting mixture was stirred at room temperature for 5 hours. The reaction mixture was poured into ice-water, neutralized with sodium carbonate and extracted with ethyl acetate. The extract was dried over anhydrous sodium sulfate and the solvent was distilled off. The resulting oil was chromatographed over silica gel (developing solvent; benzene-ethyl acetate 1:1) to give 0.37 g. of 3-cyano-2,4-dimethyl-6-nitropyridine as yellow needles melting at 52°-53° C.

0.3 g. of the pyridine thus obtained was added to 0.6 ml. of conc. sulfuric acid and the resulting mixture was stirred at 100° C. for 1 hour. The reaction mixture was poured into ice-water, made alkaline with aqueous sodium hydrogencarbonate and extracted with ethyl acetate. The extract was dried over anhydrous sodium sulfate and the solvent was distilled off to give 0.25 g. of yellow crystals, which were then recrystallized from ethyl acetate - n-hexane to give 0.2 g. of the desired product as white needles.

M.P. 179° - 180° C.

According to another aspect of this invention, novel compositions are provided in which a pyridine derivative (I) is present as an active ingredient. Such compositions comprise the pyridine derivative intimately dispersed in or admixed with an inert carrier. The term "inert carrier" as used herein means one that is substantially non-reactive with the active ingredient, orally ingestable and tolerated by the poultry.

The amount of pyridine derivative required for control of coccidiosis in poultry will vary somewhat with the specific compound employed, the species of animals, the method or the object of application or with the symptoms. Generally, the pyridine derivatives (I) are effective in preventing the disease without undesirable side effect and toxic effect when administered at a level of more than about 0.004% by weight of the feed. For good prophylactic results, it is preferred that the feed contains between about 0.004 and 0.025% by weight of the active ingredient more preferably between about 0.0075 and 0.0125%. When the pyridine derivatives are to be employed for therapeutic purpose, the higher levels are used for shorter period of time. Thus, the concentrations of about 0.05% to about 0.1% by weight of the feed may be advantageously administered for treatment of coccidiosis. When these compounds are to be employed for therapeutic purpose, it is desirable to employ the lowest levels that exhibit anticoccidial activities, in order to eliminate any risk of side effects that may appear on prolonged feeding.

In preparing solid compositions, a uniform dispersion of the active ingredient throughout the carrier can be readily accomplished by the conventional methods of grinding, stirring or milling.

Many of these pyridine activities are advantageously administered to poultry by way of the drinking water of the birds. This method of treatment may often be employed in the therapeutic use, since poultry with coccidiosis are apt to consume less solid feed than normal birds.

According to still another aspect of this invention, novel compositions are provided in which active ingredient is present in relatively large amounts and which are suitable for addition to the poultry feed directly or after intermediate dilution step. Such compositions which are a preferred feature of this invention are the so-called feed supplements of permix. Representative examples of the carriers to be employed in this invention are solid oral carriers such as distillers dried grains, corn, starch, potato starch, fermentation residues, ground oyster shells. Attapulgus clay, rice bran, wheat bran, wheat middling, molasses solubles, corn mean, edible vegetable substances, soybean cake, soybean meal, antibiotic mycelis, crushed lime stone and the like. Formulation containing from about 5% to about 30% by weight, and preferably from about 10 - 25% by weight, of the active ingredient are particularly suitable for this purpose. It is preferably in the industry to use about 1 - 3 kg. of such a supplement per ton of feed.

According to another aspect of this invention, the present composition may preferably include other known anticoccidial agents to broaden its anticoccidial spectrum and, sometimes, expect a synergistic effect.

Suitable examples of such anticoccidial agents include, for example, sulfa drugs, e.g., Sulfachloropyrazine, Sulfadimethoxine, sulfaquinoxaline; thiamine derivatives, e.g., Beclotiamine, Amprolium, Dimethialium; quinoline derivatives, e.g., Buquinolate, Decoquinate, Methyl Benzoquate; folic acid antagonistic substances, e.g., pyrimethamin, Diaveridine; antibiotics, e.g., Monensin; Zolene (3,5-dinitro-o-toluamide), Clopidol (3,5-dichloro-2,6-dimethyl-4-pyridinol), Robenzidine; and the like.

The formulation of the compounds and the coccidiostatic activity of the compounds are more fully illustrated by the non-limiting examples as follows.

In these examples, all the parts are given by weight unless otherwise indicated.

The following are three typical formulations for feed supplements in accordance with the present invention:

| Formulation A | parts by weight |
|---|---|
| 2-nitroisonicotinamide | 25 |
| wheat bran | 75 |

| Formulation B | parts by weight |
|---|---|
| 6-methyl 2-nitroisonicotinamide | 20 |
| rice bran | 80 |

| Formulation C | parts by weight |
|---|---|
| N-methyl 2-nitroisonicotinamide | 10 |
| soybean meal | 90 |

The coccidiostatic activity of the pyridine derivatives (I) of this invention is determined by the following method:

Test Procedures (1) Chicks: Fourteen-day-old White Leghorn males (after hatched, fed a diet containing no anticoccidial agent and isolated as far as possible from the risk of extraneous coccidial infections) were used.

Each group consisted of 10 chicks so as to avoid the difference of mean weight (significance level, 5%).

(2) Infections: Each chick was inoculatd orally into the crop with 42,000 sporulated oocysts of *Eimeria tenella.*

(3) Concentration of tested compounds: Each tested compound as indicated below was mixed to the commercially available mixed feed at the concentration of 200 ppm.

(4) Test procedures: The above chicks were isolated from those suffering coccidiosis and observed on their states of health. Normal healthy chicks were weighed and divided into groups, each consisting of 10 chicks so as to avoid the significant difference of average body weight (significance level 5%). On the other hand, two control groups of infected and non-medicated chicks and non-infected and non-medicated ones were separately prepared. After dividing into groups, a given number of oocysts was inoculated to all groups except for the non-infected and non-medicated control group, simultaneously with the feeding of a diet containing the test compound. Two control groups were fed with a diet which has the same formula (the same lot) and no test compound.

(5) Evaluation: They are weighed from the beginning of the test to the end (when administered and infected) constantly. Daily oocyst outputs are determined as oocysts per gram feces during a period from days 4 to 6 after infection. The daily samples from each treatment are pooled and recorded as a percentage to that of the infected and non-medicated control. After 7 days from the infection, all chicks are sacrificed and the degree of the lesion of ceca are indicated as a 0 to 4 visual scale and determined by the method of Johnson and Reid described in Experimental Parasitology vol. 28, 30 - 36 pp., (1970).

Evaluation item's values are calculated according to the following equations, respectively.

i. Rate of oocyst production (%)

$$= \frac{\text{Oocyst outputs of each group}}{\text{Oocyst outputs of infected and non-medicated group}} \times 100$$

The accumulated oocyst outputs per gram feces, on 6 or 7 days after infection, is defined as "oocyst number".

ii. Relative rate of weight gain (%)

$$= \frac{\text{Average weight gain of each group}}{\text{Average weight gain of non-infected and non-medicated group}} \times 100$$

The total of the weight gain from the beginning of the test to the end divided with the number of the chicks is defined as "average weight gain".

iii. Mean lesion score of cecum $$= \frac{\text{Total cecum lesion of scores}}{\text{Number of chicks}}$$

iv. Mortality $$= \frac{\text{Number of chicks at the end of test}}{\text{Number of chicks at the beginning of test}} \times 100$$

The results are listed in the following Table.

Table

| Compound No. | Rate of oocyst production (%) | Relative rate of weight gain (%) | Mean lesion score of cecum | Mortality (%) |
|---|---|---|---|---|
| 1 | 0 | 98.5 | 0 | 0 |
| 3 | 0.5 | 89.0 | 0.9 | 0 |
| 4 | 0 | 97.0 | 0 | 0 |
| 5 | 0 | 97.2 | 0 | 0 |
| 6 | 8.9 | 78.9 | 2.0 | 0 |
| 11 | 0 | 97.0 | 0 | 0 |

Table-continued

| Compound No. | Rate of oocyst production (%) | Relative rate of weight gain (%) | Mean lesion score of cecum | Mortality (%) |
|---|---|---|---|---|
| 13 | 1.1 | 90.9 | 0.5 | 0 |
| 17 | 1.5 | 94.3 | 0.4 | 0 |
| 21 | 0 | 98.6 | 0 | 0 |
| 24 | 0 | 98.7 | 0 | 0 |
| 35 | 0 | 98.5 | 0 | 0 |
| 47 | 0.5 | 94.6 | 0.5 | 0 |
| 56 | 0.1 | 99.0 | 0.2 | 0 |
| 57 | 0 | 100 | 0 | 0 |
| 58 | 0 | 99.9 | 0 | 0 |
| 61 | 0 | 99.3 | 0 | 0 |
| 65 | 0 | 98.9 | 0 | 0 |
| 52 | 0 | 97.8 | 0 | 0 |
| 74 | 0 | 97.5 | 0 | 0 |
| 78 | 0.5 | 92.0 | 1.0 | 0 |
| 80 | 1.2 | 89.0 | 1.2 | 0 |
| 84 | 0 | 99.0 | 0 | 0 |
| 85 | 0.2 | 91.7 | 0.1 | 0 |
| 88 | 0 | 98.5 | 0 | 0 |
| 96 | 0 | 95.5 | 0 | 0 |
| 97 | 0 | 95.0 | 0 | 0 |
| 105 | 0 | 98.4 | 0 | 0 |
| 143 | 0.4 | 91.8 | 0.1 | 0 |
| 162 | 0 | 95.0 | 0 | 0 |
| 205 | 0 | 92.7 | 0 | 0 |
| 213 | 1.2 | 90.5 | 1.1 | 0 |
| 214 | 0.1 | 91.0 | 0.2 | 0 |
| 226 | 0 | 92.5 | 0.2 | 0 |
| 227 | 0.6 | 90.2 | 1.0 | 0 |
| 360 | 2.6 | 90.0 | 1.8 | 0 |
| 367 | 12.6 | 87.0 | 1.8 | 0 |
| 379 | 3.9 | 89.0 | 1.2 | 0 |
| Infected-non-medicated control | 100 | 50 | 4.0 | 30 |
| Uninfected-non-medicated control | 0 | 100 | 0 | 0 |

It will be evident from the above results that the pyridine derivatives of the abovementioned formula (I) possess an extremely high degree of activity which cause coccidiosis, accompanying with good weight gain of the poultry without any unfavorable side effects.

What is claimed is:

1. A compound having the formula

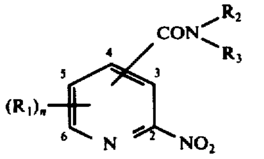

wherein $R_1$ is an alkyl group having 1 to 3 carbon atoms;

$R_2$ is hydrogen atom or an alkyl group having 1 to 3 carbon atoms;

$R_3$ is hydrogen atom, an alkyl group having 1 to 4 carbon atoms, an alkenyl group having 3 to 4 carbon atoms, or an alkyl group having 1 or 2 carbon atoms and hydroxy as a substituent;

$n$ is an integer of 0 to 2 inclusive; and when $n$ is 2, $R_1$'s may be the same or different;

provided that when $R_2$ is said alkyl group having 1 to 3 carbon atoms, $R_3$ is said alkyl group having 1 to 4 carbon atoms, and the group

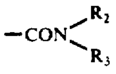

is attached to the pyridine ring at the 4- or 5-position thereof.

2. A compound according to claim 1, wherein $R_2$ is hydrogen atom or an alkyl group having 1 or 2 carbon atoms and $R_3$ is hydrogen atom, an alkyl group having 1 or 2 carbon atoms, allyl group or hydroxymethyl group; provided that when $R_2$ is said alkyl group having 1 or 2 carbon atoms, $R_3$ is said alkyl group having 1 or 2 carbon atoms.

3. A compound according to claim 1, wherein $R_2$ is hydrogen atom or an alkyl group having 1 or 2 carbon atoms and $R_3$ is hydrogen atom or an alkyl group having 1 or 2 carbon atoms; provided that when $R_2$ is said alkyl group having 1 or 2 carbon atoms, $R_3$ is said alkyl group having 1 or 2 carbon atoms.

4. A compound according to claim 1, wherein the group

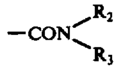

is attached to the pyridine ring at the 4-position, $n$ is 0 or 1, $R_1$ is methyl group, $R_2$ is hydrogen atom or an alkyl group having 1 or 2 carbon atoms and $R_3$ is hydrogen atom, an alkyl group having 1 or 2 carbon atoms, allyl group or hydroxymethyl group; provided that when $R_2$ is said alkyl group having 1 or 2 carbon atoms, $R_3$ is said alkyl group having 1 or 2 carbon atoms.

5. 2-Nitroisonicotinamide.

6. N-Methyl 2-Nitroisonicotinamide.

7. N-Ethyl 2-Nitroisonicotinamide.

8. N-Hydroxymethyl 2-Nitroisonicotinamide.

9. N,N-Dimethyl 2-Nitroisonicotinamide

10. N-Ethyl-N-methyl 2-Nitroisonicotinamide.

11. 6-Methyl-2-nitroisonicotinamide.

12. N-Ethyl 6-Methyl-2-nitroisonicotinamide.

13. N,N-Dimethyl 6-Methyl-2-nitroisonicotinamide.

14. 3-Methyl-2-nitroisonicotinamide.

15. 4-Methyl-6-nitronicotinamide.

16. 4-Methyl-6-nitro-2-pyridinecarboxamide.

17. N,N-Diethyl 6-Methyl-2-nitroisonicotinamide.

18. An anticoccidial composition containing an amount, sufficient to inhibit coccidiosis, of a compound having the formula

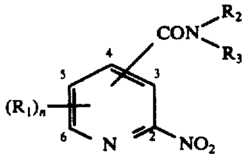

intimately dispersed in an inert carrier, wherein $R_1$ is an alkyl group having 1 to 3 carbon atoms;

$R_2$ is hydrogen atom or an alkyl group having 1 to 3 carbon atoms;

$R_3$ is hydrogen atom, an alkyl group having 1 to 4 carbon atoms, an alkenyl group having 3 or 4 carbon atoms, or an alkyl group having 1 or 2 carbon atoms and hydroxy as a substituent;

$n$ is an integer of 0 to 2 inclusive; and when $n$ is 2, $R_1$'s may be the same or different;

provided that when $R_2$ is said alkyl group having 1 to 3 carbon atoms, $R_3$ is said alkyl group having 1 to 4 carbon atoms, and the group

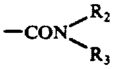

is attached to the pyridine ring at the 4- or 5-position thereof.

19. An anticoccidial composition according to claim 18 wherein $R_2$ is hydrogen atom or an alkyl group having 1 or 2 carbon atoms and $R_3$ is hydrogen atom, an alkyl group having 1 or 2 carbon atoms, allyl group or hydroxymethyl group; provided that when $R_2$ is said alkyl group having 1 or 2 carbon atoms, $R_3$ is said alkyl group having 1 or 2 carbon atoms.

20. An anticoccidial composition according to claim 18 wherein $R_2$ is hydrogen atom or an alkyl group having 1 or 2 carbon atoms and $R_3$ is hydrogen atom or an alkyl group having 1 or 2 carbon atoms; provided that when $R_2$ is said alkyl group having 1 or 2 carbon atoms, $R_3$ is said alkyl group having 1 or 2 carbon atoms.

21. An anticoccidial composition according to claim 18 wherein the group

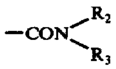

is attached to the pyridine ring at the 4-position thereof, *n* is 0 or 1, $R_1$ is methyl group, $R_2$ is hydrogen atom or an alkyl group having 1 or 2 carbon atoms and $R_3$ is hydrogen atom, an alkyl group having 1 or 2 carbon atoms, allyl group or hydroxymethyl group; provided that when $R_2$ is said alkyl group having 1 to 2 carbon atoms, $R_3$ is said alkyl group having 1 to 2 carbon atoms.

22. An anticoccidial composition according to claim 18 wherein said compound is selected from the group consisting of
2-Nitroisonicotinamide,
N-Methyl 2-Nitroisonicotinamide,
N-Ethyl 2-Nitroisonicotinamide,
N-Hydroxymethyl 2-Nitroisonicotinamide,
N,N-Dimethyl 2-Nitroisonicotinamide,
N,N-Diethyl 2-Nitroisonicotinamide,
N-Ethyl-N-methyl 2-Nitroisonicotinamide,
6-Methyl-2-nitroisonicotinamide,
N-Methyl 6-Methyl-2-nitroisonicotinamide,
N-Ethyl 6-Methyl-2-nitroisonicotinamide,
N,N-Dimethyl 6-Methyl-2-nitroisonicotinamide,
N,N-Diethyl 6-Methyl-2-nitroisonicotinamide,
3-Methyl-2-nitroisonicotinamide,
4-Methyl-6-nitronicotinamide, and
4-Methyl-6-nitro-2-pyridinecarboxamide.

23. An anticoccidial composition according to claim 18 wherein said compound is selected from the group consisting of
2-Nitroisonicotinamide,
N-Methyl 2-Nitroisonicotinamide,
N-Ethyl 2-Nitroisonicotinamide,
N-Hydroxymethyl 2-Nitroisonicotinamide,
N,N-Dimethyl 2-Nitroisonicotinamide,
N-Ethyl-N-methyl 2-Nitroisonicotinamide,
6-Methyl-2-nitroisonicotinamide,
N-Ethyl 6-Methyl-2-nitroisonicotinamide,
N,N-Dimethyl 6-Methyl-2-nitroisonicotinamide,
N,N-Diethyl 6-Methyl-2-nitroisonicotinamide,
3-Methyl-2-nitroisonicotinamide,
4-Methyl-6-nitronicotinamide, and
4-Methyl-6-nitro-2-pyridinecarboxamide.

24. An anticoccidial composition according to claim 18 wherein said compound is selected from the group consisting of
2-Nitroisonicotinamide,
N-Methyl 2-Nitroisonicotinamide,
N-Ethyl 2-Nitroisonicotinamide,
N-Hydroxymethyl 2-Nitroisonicotinamide,
N,N-Dimethyl 2-Nitroisonicotinamide,
N-Ethyl-N-methyl 2-Nitroisonicotinamide,
6-Methyl-2-nitroisonicotinamide,
N-ethyl 6-Methyl-2-nitroisonicotinamide,
N,N-Dimethyl 6-Methyl-2-nitroisonicotinamide, and
N,N-Diethyl 6-Methyl-2-nitroisonicotinamide.

25. A poultry feed having dispersed therein for control of poultry coccidiosis at least 0.005% by weight of a compound having the formula

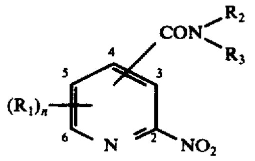

wherein $R_1$ is an alkyl group having 1 to 3 carbon atoms;

$R_2$ is hydrogen atom or an alkyl group having 1 to 3 carbon atoms;

$R_3$ is hydrogen atom, an alkyl group having 1 to 4 carbon atoms, an alkenyl group having 3 or 4 carbon atoms, or an alkyl group having 1 or 2 carbon atoms and hydroxy as a substituent;

*n* is an integer of 0 to 2 inclusive; and, when *n* is 2, $R_1$'s may be the same or different; provided that when $R_2$ is said alkyl group having 1 to 3 carbon atoms, $R_3$ is said alkyl group having 1 to 4 carbon atoms, and the group

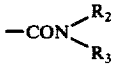

is attached to the pyridine ring at the 4- or 5-position thereof.

26. A poultry feed according to claim 25 wherein $R_2$ is hydrogen atom or an alkyl group having 1 or 2 carbon atoms and $R_3$ is hydrogen atom, an alkyl group having 1 or 2 carbon atoms, allyl group or hydroxymethyl group; provided that when $R_2$ is said alkyl group having 1 or 2 carbon atoms, $R_3$ is said alkyl group having 1 or 2 carbon atoms.

27. A poultry feed according to claim 25 wherein $R_2$ is hydrogen atom or an alkyl group having 1 or 2 carbon atoms and $R_3$ is hydrogen atom or an alkyl group having 1 or 2 carbon atoms; provided that when $R_2$ is said alkyl group having 1 or 2 carbon atoms, $R_3$ is said alkyl group having 1 or 2 carbon atoms.

28. A poultry feed according to claim 25 wherein the group

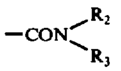

is attached to the pyridine ring at the 4-position thereof, *n* is 0 or 1, $R_1$ is methyl group, $R_2$ is hydrogen atom or an alkyl group having 1 or 2 carbon atoms and $R_3$ is hydrogen atom, an alkyl group having 1 or 2 carbon atoms, allyl group or hydroxymethyl group; provided that when $R_2$ is said alkyl group having 1 or 2 carbon atoms, $R_3$ is said alkyl group having 1 or 2 carbon atoms.

29. A poultry feed according to claim 25 wherein said compound is selected from the group consisting of
2-Nitroisonicotinamide,
N-Methyl 2-Nitroisonicotinamide,
N-Ethyl 2-Nitroisonicotinamide,
N-Hydroxymethyl 2-Nitroisonicotinamide,
N,N-Dimethyl 2-Nitroisonicotinamide,
N,N-Diethyl 2-Nitroisonicotinamide,
N-Ethyl-N-methyl 2-Nitroisonicotinamide,
6-Methyl-2-nitroisonicotinamide,
N-Methyl 6-Methyl-2-nitroisonicotinamide,
N-Ethyl 6-Methyl-2-nitroisonicotinamide,
N,N-Dimethyl 6-Methyl-2-nitroisonicotinamide,
N,N-Diethyl 6-Methyl-2-nitroisonicotinamide,
3-Methyl-2-nitroisonicotinamide,
4-Methyl-6-nitronicotinamide, and
4-Methyl-6-nitro-2-pyridinecarboxamide.

30. A poultry feed according to claim 25 wherein said compound is selected from the group consisting of
2-Nitroisonicotinamide,
N-Methyl 2-Nitroisonicotinamide,
N-Ethyl 2-Nitroisonicotinamide,
N-Hydroxymethyl 2-Nitroisonicotinamide,
N,N-Dimethyl 2-Nitroisonicotinamide,
N-Ethyl-N-methyl 2-Nitroisonicotinamide,
6-Methyl-2-nitroisonicotinamide,
N-Ethyl 6-Methyl-2-nitroisonicotinamide,
N,N-Dimethyl 6-Methyl-2-nitroisonicotinamide,
N,N-Diethyl 6-Methyl-2-nitroisonicotinamide,
3-Methyl-2-nitroisonicotinamide,
4-Methyl-6-nitronicotinamide, and
4-Methyl-6-nitro-2-pyridinecarboxamide.

31. A poultry feed according to claim 25 wherein said compound is selected from the group consisting of
2-Nitroisonicotinamide,
N-Methyl 2-Nitroisonicotinamide,
N-Ethyl 2-Nitroisonicotinamide,
N-Hydroxymethyl 2-Nitroisonicotinamide,
N,N-Dimethyl 2-Nitroisonicotinamide,
N-Ethyl-N-methyl 2-Nitroisonicotinamide,
6-Methyl-2-nitroisonicotinamide,
N-Ethyl 6-Methyl-2-nitroisonicotinamide,
N,N-Dimethyl 6-Methyl-2-nitroisonicotinamide, and
N,N-Diethyl 6-Methyl-2-nitroisonicotinamide.

* * * * *